United States Patent
Gabetta et al.

(10) Patent No.: US 7,112,687 B2
(45) Date of Patent: Sep. 26, 2006

(54) METHODS FOR OBTAINING PACLITAXEL FROM TAXUS PLANTS

(75) Inventors: Bruno Gabetta, Milan (IT); Gianfranco Zini, Milan (IT)

(73) Assignee: Indena, S.p.A., Milan (IL)

( * ) Notice: Subject to any disclaimer, the term of this patent is extended or adjusted under 35 U.S.C. 154(b) by 151 days.

(21) Appl. No.: 10/893,862

(22) Filed: Jul. 15, 2004

(65) Prior Publication Data

US 2006/0014968 A1    Jan. 19, 2006

(51) Int. Cl.
*C07D 305/00* (2006.01)
*C07D 407/00* (2006.01)
*C07D 493/00* (2006.01)

(52) U.S. Cl. ........................ 549/510; 549/511
(58) Field of Classification Search ................ 549/510, 549/511
See application file for complete search history.

(56) References Cited

U.S. PATENT DOCUMENTS 5,475,120 A * 12/1995 Rao ........................... 549/510
6,333,419 B1 * 12/2001 Gabetta et al. ............. 549/510

* cited by examiner

*Primary Examiner*—Thomas McKenzie
*Assistant Examiner*—Niloofar Rahmani
(74) *Attorney, Agent, or Firm*—Jones Day (57) ABSTRACT

Methods for obtaining paclitaxel from plants containing paclitaxel are disclosed. Plant material is first obtained from plants containing paclitaxel. Paclitaxel is then extracted from the plant material. Subsequently, paclitaxel is separated from the paclitaxel extract using a series of column chromatography separation steps to obtain at least one fraction containing paclitaxel. The paclitaxel in a fraction that is obtained from the final chromatography step is crystallized. Using these methods, high purity paclitaxel may be efficiently obtained from plants containing paclitaxel.

52 Claims, 1 Drawing Sheet

FIGURE 1

Methods for Obtaining Paclitaxel From Plants Containing Paclitaxel

METHODS FOR OBTAINING PACLITAXEL FROM TAXUS PLANTS

FIELD OF THE INVENTION

This invention relates generally to methods for obtaining paclitaxel from plants containing paclitaxel. More particularly, the invention is directed to methods of extracting paclitaxel from plants of the Taxaceae family, which includes plants of the genus *Taxus*, such as *Taxus media*, involving a series of column chromatography steps followed by crystallization of paclitaxel.

BACKGROUND OF THE INVENTION

Paclitaxel is an anticancer compound primarily derived from the bark of the *Taxus brevifolia* (Pacific yew) tree. In the 1960's, the National Cancer Institute began a study of plant extracts exhibiting anti-cancer or anti-neoplastic activities. The crude extract of bark from the *Taxus brevifolia* was found to inhibit a variety of tumors. In 1971, paclitaxel was isolated and described by M. C. Wani et al. (*J. Am. Chem. Soc.* 93, 2325, (1971)), who defined the structure of paclitaxel using chemical methods and X-ray crystallographic analysis. In 1979, Schiff and coworkers demonstrated paclitaxel's novel mechanism of action. This mechanism includes binding to microtubules and preventing their depolymerization under conditions where depolymerization would normally occur. Paclitaxel is currently used in the treatment of ovarian, breast and non-small cell lung cancers.

Although Paclitaxel is a natural product primarily extracted from the bark of the Pacific yew (*T. brevifolia*), it is also found in other members of the Taxaceae family including *T. canadensis* and *T. yunnanensis*. Paclitaxel is also present in the epigeal parts and roots of other yew species, including the European yew (*T. baccata*), whose needles contain paclitaxel and analogs, Asian yews (*T. wallichiana* and *T. chinensis*), and yew trees cultivated for ornamental purposes. The following varieties of *Taxus cultivars* have also been found to contain paclitaxel: *T.x media* "Henryi," *T.x media* "Runyan," *T. cuspidata, T.x media* "Halloran," *T.x media* "Hatfield," *T.x media* "Hicksii," *T.x media* "Tauntonii," *T.x media* "Dark Green Spreader," *T.x media* "Wardii," *T.x media* "Brownii," *T.x media* "Densiformis," *T.x media* "Nigra," *T.x cuspidata* "Brevifolia," and *T. cuspidata* "Spreader."

All of these species contain paclitaxel in very limited amounts. For example, the bark of *T. brevifolia* and *T. yunnanensis* trees contains about 0.02% paclitaxel and the needles and roots of *T. media* Hicksii shrubs contain between about 0.005% to about 0.1% paclitaxel.

Therefore, it is of great interest to develop efficient methods of extracting high purity paclitaxel from plant material. The present invention provides methods for extracting high purity paclitaxel from plant material using chromatography followed by crystallization of the paclitaxel.

SUMMARY OF THE INVENTION

Therefore, an object of the present invention is to provide methods for obtaining high purity paclitaxel from plants containing paclitaxel. These methods have the advantages of assuring the stability of paclitaxel, allowing the use of various *Taxus cultivar* or part of it, independent of the content of paclitaxel, and allowing the maximum recovery of the paclitaxel present in the biomass. The methods described in the present invention provide several advantages over previous methods. For example, it is known that paclitaxel can suffer degradation reactions such as epimerization in position 7, deacetylation in position 10, and detachment of the side chain in position 13. These degradation reactions, which affect both the quality and yield of the isolated paclitaxel, arise from heating, especially in media containing large amounts of alcoholic solvents. In the methods described in the present invention, alcohols are used in limited amounts and in diluted conditions and generally no heating is involved during the extraction process. Hence, the methods described herein enhance the stability of paclitaxel.

Furthermore, the methods described herein can use various types of plant parts as starting materials. More specifically, the starting material used in the present invention can be the leaves, stems, branches, bark, roots alone or mixtures thereof from a paclitaxel-containing plant. The starting material can be chosen independent of the ratio of the plant parts, the nature of the *Taxus cultivar* and the content of paclitaxel. The methods of the present invention provide the same process efficiency and assure a constant and high quality of paclitaxel. Also, the methods described herein allow for high yields of paclitaxel.

These methods comprise preparing a paclitaxel extract by extracting paclitaxel from a plant material. Paclitaxel is separated from the paclitaxel extract using column chromatography systems, wherein each column chromatography system comprises a stationary phase and an eluting solvent, and crystallizing the paclitaxel contained in at least one fraction obtained in the final chromatography step. In some embodiments, the paclitaxel is crystallized from all fractions obtained from the final chromatography step. The resulting paclitaxel crystals may be dried. As described above, several biomasses can be used as starting plant material. If *Taxus media* whole plants are used as biomass, the plant material is typically composed of about 40 to about 60 weight (w/w) percent aerial parts and about 60 to about 40 w/w percent roots. Additionally, the stationary phase and eluting solvent may differ between different systems.

In the methods of the present invention, paclitaxel is extracted from a plant material to form a paclitaxel extract. Paclitaxel may be extracted from the plant material using a solvent, such as a combination of water and an organic solvent. Column chromatography systems are used to separate the paclitaxel from the paclitaxel extract by obtaining at least one fraction containing paclitaxel after each chromatographic separation and, optionally, subjecting the at least one fraction to reduced pressure to remove the eluting solvent. When more than one fraction is collected following each separation, at least some of the fractions containing paclitaxel can be combined before removing the eluting solvent from this combination. Additionally, crystallizing may occur over a 24 hour period and it may occur at room temperature. The present invention further provides a method for extracting paclitaxel from *Taxus media* by extracting the plant material with an aqueous solution comprising about 40 to about 60 volume (v/v) percent acetone at room temperature. In one embodiment, the methods of the present invention comprise preparing a paclitaxel extract by extracting paclitaxel from a plant material and then separating paclitaxel from the paclitaxel extract using a first column chromatography system comprising a first stationary phase and a first eluting solvent to obtain at least one fraction containing paclitaxel. Paclitaxel is then separated from the at least one fraction using a second column chromatography system comprising a second stationary phase and a second eluting solvent to obtain at least one fraction containing paclitaxel. Thereafter, paclitaxel is separated from the at least one fraction using a third column chromatography system comprising a third stationary phase and a third eluting solvent to obtain at least one fraction containing paclitaxel. Furthermore, paclitaxel is separated from the at least one fraction using a fourth column chromatography system comprising a fourth stationary phase and a fourth eluting solvent to remove at least cephalomannine and to obtain at least one fraction containing paclitaxel. The paclitaxel is them crystallized from the at least one fraction using a crystallizing solvent to obtain paclitaxel crystals.

In another embodiment, the methods of the present invention comprise preparing a paclitaxel extract by extracting paclitaxel from a plant material. Paclitaxel is then separated from the paclitaxel extract by using a first column chromatography system comprising a first stationary phase and a first eluting solvent to obtain at least one fraction containing paclitaxel and removing the first eluting solvent from the at least one fraction to form a first residue. Thereafter, paclitaxel is separated from the first residue by using a second column chromatography system comprising a second stationary phase and a second eluting solvent to obtain at least one fraction containing paclitaxel from the first residue, and then removing the second eluting solvent from the at least one fraction to form a second residue. Subsequently, paclitaxel is separated from the second residue by using a third column chromatography system comprising a third stationary phase and a third eluting solvent to obtain at least one fraction containing paclitaxel from the second residue, and then removing the third eluting solvent from the at least one fraction to form a third residue. Paclitaxel is then separated from the third residue by using a fourth column chromatography system comprising a fourth stationary phase and a fourth eluting solvent to obtain at least one fraction containing paclitaxel from the third residue, and then removing the fourth eluting solvent from the third residue to form a fourth residue. The paclitaxel is then crystallized from the fourth residue using a crystallizing solvent to obtain paclitaxel crystals.

In another embodiment, the methods of the present invention comprise preparing a plant material extract from the *Taxus media* by extracting the plant material with an aqueous solvent comprising about 40 to about 60 v/v percent acetone at room temperature and then preparing a paclitaxel extract by extracting paclitaxel from the plant material extract. Paclitaxel is then separated from the paclitaxel extract comprising using a first chromatography system comprising silica gel as a stationary phase and an eluting solvent comprising dichloromethane alone or a mixture of dichloromethane and methanol to obtain at least one fraction containing paclitaxel. The at least one fraction is then subjected to reduced pressure to remove the dichloromethane and/or methanol. Paclitaxel is then separated from the at least one fraction by using a second column chromatography system comprising neutral alumina as a stationary phase and as an eluting solvent comprising acetone to obtain at least one fraction containing paclitaxel, and then subjecting the at least one fraction to reduced pressure to remove the acetone. Thereafter, paclitaxel is separated from the at least one fraction by using a third column chromatography system comprising silica gel as a stationary phase and an eluting solvent comprising a mixture of n-hexane and acetone and to obtain at least one fraction containing paclitaxel, and then subjecting the at least one fraction to reduced pressure to remove the n-hexane and acetone. Moreover, paclitaxel is separated from the at least one fraction by using a fourth column chromatography system comprising silica gel as a stationary phase and an eluting solvent comprising t-butyl acetate to remove at least cephalomannine and to obtain at least one fraction containing paclitaxel, and subjecting the at least one fraction to reduced pressure to remove the t-butyl acetate. The at least one fraction is crystallized over a 24 hour period using a mixture of cyclohexane and acetone as the crystallizing solvent at room temperature to obtain paclitaxel crystals. Thereafter, the paclitaxel crystals are dried under vacuum for 48 hours.

In another embodiment, the methods of the present invention comprise preparing a plant material extract from the *Taxus media* by extracting the plant material with an aqueous solvent comprising about 40 to about 60 v/v percent acetone at room temperature and then preparing a paclitaxel extract by extracting paclitaxel from the plant material extract. Paclitaxel is then separated from the paclitaxel extract by using a first chromatography system comprising silica gel as a stationary phase and eluting solvent comprising dichloromethane and methanol to obtain at least one fraction containing paclitaxel and then subjecting the at least one fraction to reduced pressure to obtain a residue, and then dissolving the residue in acetone to obtain an acetone-residue composition. Subsequently, paclitaxel is separated from the acetone-residue composition by using a second column chromatography system comprising neutral alumina as a stationary phase and an eluting solvent comprising acetone to obtain at least one fraction containing paclitaxel. The at least one fraction is subjected to reduced pressure to remove the acetone. Paclitaxel is then separated from the at least one fraction by using a third column chromatography system comprising silica gel as a stationary phase and an eluting solvent comprising n-hexane and acetone to obtain at least one fraction containing paclitaxel, and subjecting the at least one fraction to reduced pressure to remove the n-hexane and acetone. Paclitaxel is separated from the at least one fraction by using a fourth column chromatography system comprising silica gel as a stationary phase and an eluting solvent comprising t-butyl acetate to remove at least cephalomannine and to obtain at least one fraction containing paclitaxel, and subjecting the at least one fraction to reduced pressure to remove the t-butyl acetate. The at least one fraction is crystallized over a 24 hour period using a mixture of cyclohexane and acetone as the crystallizing solvent at room temperature to obtain paclitaxel crystals. The paclitaxel crystals are dried under vacuum for 48 hours.

In one embodiment, the methods of the present invention comprise preparing a plant material extract from the *Taxus media* by extracting the plant material with an aqueous solution comprising about 40 to about 60 v/v percent acetone at room temperature and preparing a paclitaxel extract by extracting paclitaxel from the plant material extract. Paclitaxel is separated from the paclitaxel extract by using a first chromatography system comprising neutral alumina as a stationary phase and an eluting solvent comprising dichloromethane and methanol to obtain at least one fraction containing paclitaxel and subjecting the at least one fraction to reduced pressure to remove the dichloromethane and methanol. The paclitaxel is separated from the at least one fraction by using a second column chromatography system comprising silica gel as a stationary phase and an eluting solvent comprising dichloromethane and methanol to obtain at least one fraction containing paclitaxel, and subjecting the at least one fraction to reduced pressure to obtain a residue, and dissolving the residue in acetone to obtain an acetone-residue composition. Thereafter, paclitaxel is separated from the acetone-residue composition by using a third column chromatography system comprising silica gel as a stationary phase and an eluting solvent comprising n-hexane and acetone to obtain at least one fraction containing paclitaxel, and subjecting the at least one fraction to reduced pressure to remove the mixture of n-hexane and acetone. Subsequently, paclitaxel is separated from the at least one fraction by using a fourth column chromatography system comprising silica gel as a stationary phase and an eluting solvent comprising a t-butyl acetate to remove at least cephalomannine and to obtain at least one fraction containing paclitaxel, and subjecting the at least one fraction to reduced pressure to remove the t-butyl acetate. Thereafter, the at least one fraction is crystallized over a 24 hour period using a mixture of cyclohexane and acetone as the crystallizing solvent at room temperature to obtain paclitaxel crystals. The paclitaxel crystals are dried under vacuum for 48 hours.

DETAILED DESCRIPTION OF THE INVENTION

Figure 1:
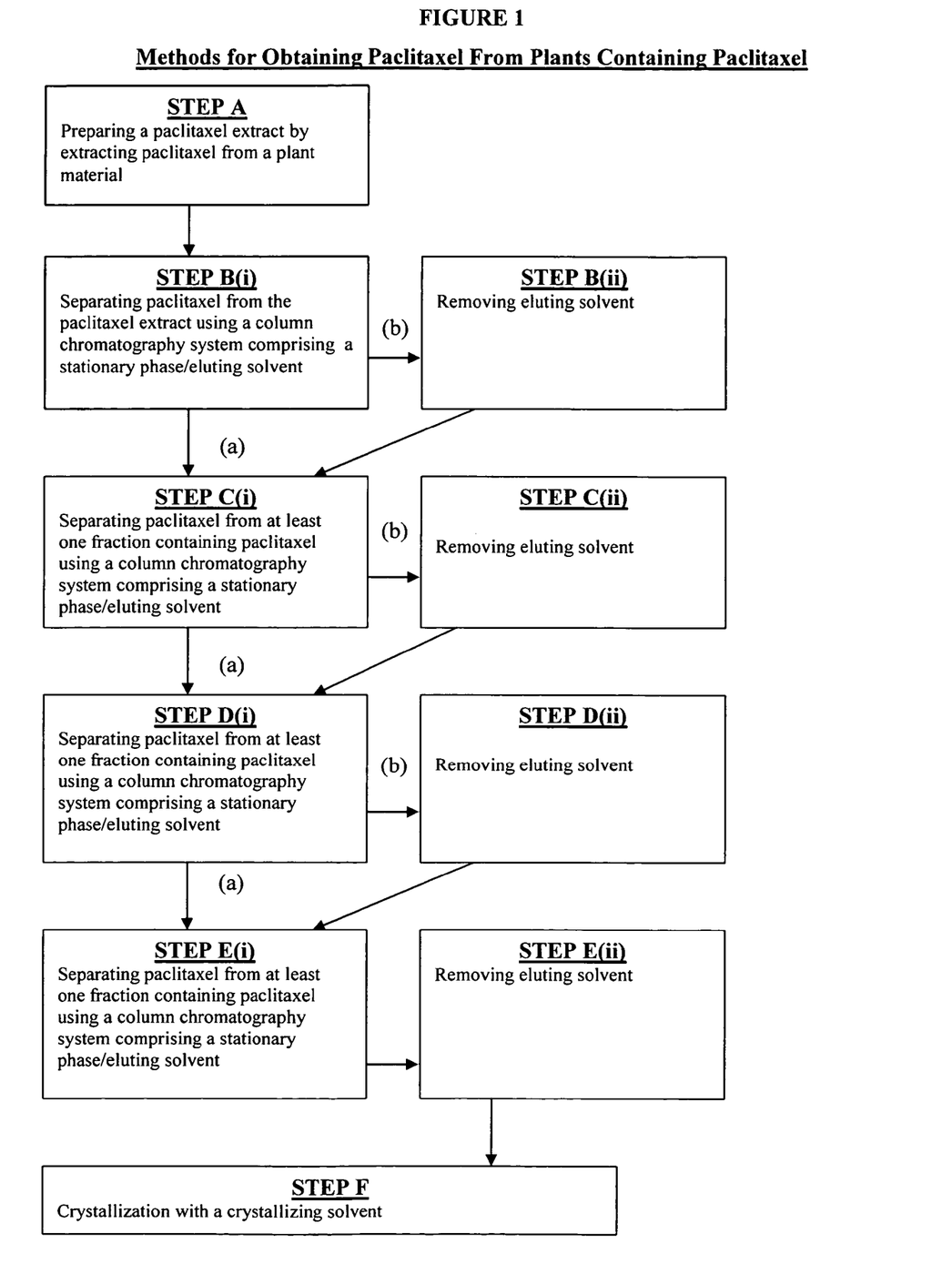
FIG. 1 is a flow diagram outlining an embodiment of the methods of the present invention.

The methods of the present invention include a method for obtaining paclitaxel from plants containing paclitaxel. FIG. 1 shows a flow diagram outlining steps of an embodiment of the methods of the present invention. Step A comprises preparing a paclitaxel extract by extracting paclitaxel from a plant material containing paclitaxel. The paclitaxel is then separated from the other constituents in the paclitaxel extract in Steps B–E using column chromatography separation systems. Each step marked with (i) involves separating paclitaxel from the paclitaxel extract or chromatographic fraction using a column chromatography system comprising a stationary phase and an eluting solvent to obtain at least one fraction containing paclitaxel. Each step marked with (ii) comprises removing the eluting solvent from the at least one fraction obtained in the previous chromatography step. In a preferred embodiment, the at least one fraction is subjected to reduced pressure to remove the eluting solvent. Labels (a) and (b) in FIG. 1 designate alternative separation routes. For instance, if route (a) is followed for each separation step, the eluting solvent is not removed from the at least one fraction of paclitaxel. In contrast, if route (b) is used for each separation step, the eluting solvent is removed from the at least one fraction of paclitaxel. In certain embodiments, route (a) can be followed for certain of the separation steps and route (b) can be followed for other separation steps. For example in Step B, route (b) can be taken so that the eluting solvent is removed from the fraction obtained in Step B whereas in Step C, route (a) is taken so that the fraction is directly subjected to separation in Step D, without removal of the eluting solvent of Step C. Step F involves crystallizing the at least one fraction obtained from the final chromatography step. In a specific embodiment, the at least one fraction obtained from Step E(ii) is crystallized in Step F. Although only four chromatography steps are shown in FIG. 1, there can be additional chromatography steps before crystallization. The crystallization step can be followed by a drying step.

The Plant Material

The starting material for use in Step A of the present invention is plant material containing paclitaxel. Suitable plant material can be obtained from the plant parts of the Taxaceae family, i.e. *Taxus* plant. Preferably, the plant material is prepared from *Taxus media*. Suitable varieties of *Taxus media* include *T.x media* "Hill," *T.x media* "Henryi," *T.x media* "Runyan," *T. cuspidata, T.x media* "Halloran," *T.x media* "Hatfield," *T.x media* "Hicksii," *T.x media* "Tauntonii," *T.x media* "Dark Green Spreader," *T.x media* "Wardii," *T.x media* "Brownii," *T.x media* "Densiformis," *T.x media* "Nigra," *T.x cuspidata* "Brevifolia," and *T.x cuspidata* "Spreader." Further, the plant material can be prepared from various parts of a *Taxus* plant, such as fresh or dry roots, leaves, branches, seeds, bark, stems or mixtures thereof. Preferably, the plant material is prepared from about 40 to about 60 w/w percent aerial parts and about 60 to about 40 w/w percent roots. The plant material is obtained from a paclitaxel-containing plant part by, for example, extracting, crushing or cutting. In a specific embodiment, the plant material to be extracted is ground using a blade milling line, equipped, for instance, with a 10 mm diameter net. In one embodiment, the plant material is extracted using at least one extraction solvent. Suitable solvents include aqueous solvents, such as, aqueous organic solvents, e.g. acetone in water. Preferably, a mixture of about 40 to about 60 volume percent acetone and about 60 to about 40 volume percent water is used. Aqueous acetone can prevent degradation of the paclitaxel. Preferably, extraction takes place at room temperature. Extraction at room temperature can prevent degradation of paclitaxel.

Extraction of Paclitaxel and Cogeners

Prior to the first chromatography step, e.g. Step B, an extract of paclitaxel is prepared such as in Step A. In one embodiment, the paclitaxel extract is prepared by extracting the paclitaxel from the plant material with a solvent. In a specific embodiment, the paclitaxel extract is prepared by treating an aqueous acetone extract of the plant material. Suitable extraction solvents include without limitation aliphatic esters, such as ethyl acetate, or chlorinated solvents, such as chloroform or dichloromethane. A preferred extraction solvent is dichloromethane. In a specific embodiment, before the paclitaxel is extracted with one of the above solvents, the aqueous acetone extract is concentrated under vacuum to eliminate the acetone. The concentrate can then be diluted with a solvent. This dilution solvent can include methyl alcohol or other hydrosoluble alcoholic solvents such as ethyl or propyl alcohol. Paclitaxel is then extracted from the diluted concentrate using an extraction solvent such as dichloromethane and the other extraction solvents discussed above. A paclitaxel extract is formed.

In one embodiment, the paclitaxel extract is concentrated, under vacuum, in order to eliminate the solvents. The concentrated paclitaxel extract contains paclitaxel and its cogeners, chlorophylls, fats, lignans, flavonoids, phenols and various polar impurities. Cogeners include, for example, cephalomannine, N-debenzoyl-N-hexanoyl-paclitaxel, N-debenzoyl-N-hexanoyl-N-methyl-paclitaxel, N-debenzoyl-N-phenylacetyl-paclitaxel, N-debenzoyl-N-cinnamoyl-paclitaxel, and 2-debenzoyl-2-tigloyl-paclitaxel. Each of these may be accompanied by the respective 7-epi, 10-deacetyl and 7-0-xylosyl derivative. The corresponding latter derivatives of paclitaxel are also present. These non-paclitaxel constituents or impurities can be removed using chromatography techniques as discussed below.

Purification of Paclitaxel by Chromatography

Paclitaxel is separated from the paclitaxel extract by the application of at least 4 column chromatography steps designated in FIG. 1 as Steps B–E. Steps B(i)–E(i) each include the use of a chromatography system comprising a stationary phase and an eluting solvent. Each system can be the same apparatus with a different stationary phase and eluting solvent. Suitable stationary phases include without limitation neutral alumina and silica-gel. Possible eluting solvents include without limitation acetone, dichloromethane, methanol, n-hexane, t-butyl acetate, chloroform, and ethyl acetate.

Each chromatography step includes using a column chromatography system comprising a stationary phase and an eluting solvent to obtain at least one fraction containing paclitaxel. At least one fraction may include a combination of multiple fractions obtained from a chromatography step. For instance, more than one fraction can be obtained from a chromatography step. These fractions are then combined and the next chromatography step is performed on the combined fractions.

In one embodiment, the eluting solvent is removed from at least one fraction. At least one fraction may be subjected to reduced pressure in Steps B(ii)–E(ii) to remove the eluting solvent. Removing the solvent can include just a portion of the solvent, not necessarily all the solvent in the at least one fraction.

In one embodiment, the first chromatography step, Step B(i), generally separates fats, chlorophylls, low-molecular weight phenolics and very polar impurities from the paclitaxel. The second chromatography step, Step C(i), generally separates additional impurities, in particular flavonoids and lignans from the paclitaxel. The third chromatography step, Step D(i), generally separates other taxanes from paclitaxel. Such taxanes include the above-mentioned taxane derivatives, in particular, cephalomannine and minor amounts of the other taxanes, such as those discussed above. The fourth chromatography step, Step E(i), separates the cogener cephalomannine from the paclitaxel. Suitable stationary phases for removing cephalomannine include silica gel. Examples of useful eluting solvents include t-butyl acetate, i-butyl acetate, n-butyl formate, i-butyl formate, t-butyl formate, and s-butyl formate. See U.S. Pat. No. 6,333,419, the contents of which are herein incorporated by reference in their entirety.

In one embodiment, the first column chromatography system comprises a stationary phase comprising silica gel and an eluting solvent comprising methylene chloride followed by a mixture of methylene chloride-methanol in 99:1 or 98:2 v/v ratio. In another embodiment, the second column chromatography system comprises a stationary phase comprising neutral alumina and an eluting solvent comprising acetone. In yet another embodiment, the third column chromatography system comprises a stationary phase comprising silica gel and an eluting solvent comprising n-hexane and acetone in a ratio of 4:1 v/v. In another embodiment, the fourth column chromatography system comprises a stationary phase comprising silica gel and an eluting solvent comprising t-butyl acetate.

Optionally, it is also possible to eliminate the impurities in a different order. For example, the removal of phenolics over alumina can be performed before the elimination of chlorophylls and fats using silica gel as the stationary phase.

Crystallization of Paclitaxel

Following the final chromatography step, the at least one fraction containing paclitaxel that is obtained from that step is crystallized in Step F using a crystallizing solvent to obtain paclitaxel crystals. Suitable crystallizing solvents include cyclohexane, acetone, n-hexane, i-hexane, n-heptane, t-butyl acetate and mixtures thereof. Preferably, a mixture of cyclohexane and acetone in a ratio of 1:1 is used. In one embodiment, the crystallization occurs at room temperature. Generally, the crystallization occurs over a 24 hour period. However, crystallization can also occur over other time periods. Following crystallization, the paclitaxel crystals are then dried under vacuum at a temperature, such as between about 50° and about 60° C. Preferably, the crystals are dried for about 48 hours.

EXAMPLE 1

One ton of dried and ground plant material obtained from the *T. media* Hicksii composed of about 500 kg roots and about 500 kg leaves and twigs was extracted at room temperature with 15,000 L of 50% aqueous acetone. The extract was concentrated under vacuum to about 300 L. Then, 150 L of methanol was added and five extractions with 200 L of dichloromethane were carried out. The pooled organic layers were concentrated under vacuum until a soft residue was obtained, which was redissolved in dichloromethane and column chromatographed over 180 kg of silica gel. About 2,700 L of dichloromethane were eluted through the column and discarded.

Paclitaxel was then eluted with a mixture of dichloromethane-methanol 99:1 (v/v). The solution was then evaporated under vacuum in order to obtain a soft residue. The residue was dissolved in 8 L of acetone to obtain an acetone-residue which was passed through a column containing 30 kg of neutral alumina, eluting with the same solvent. Fractions containing paclitaxel were pooled and concentrated under vacuum to 8 L.

The acetone solution was then charged on a column containing 180 kg of silica gel packed with the mixture of n-hexane-acetone 4:1. Elution with this eluent provided paclitaxel free of most of the other taxanes, except cephalomannine. Fractions containing paclitaxel were pooled and concentrated under vacuum to 5 L.

The solution was then chromatographed over 180 kg of silica gel packed with t-butyl acetate, eluting with this solvent. Fractions containing paclitaxel were pooled and evaporated under vacuum until a soft residue was obtained. Further elution of the columns with t-butyl acetate removed at least cephalomannine. The soft residue (about 300 g) containing paclitaxel was dissolved in 2 L of acetone, diluted with 1.2 L of cyclohexane and left to crystallize. After filtration and drying at 50° C. for 48 hours, 255 g of paclitaxel having a purity greater than 99% were obtained.

EXAMPLE 2

One hundred kilograms of dried and ground plant material from *Taxus media* dark green spreader whole plant composed of about 40 kg roots and about 60 kg leaves and twigs were extracted at room temperature with 1,500 L of 50% aqueous acetone. The extract was concentrated under vacuum to 30 L. Then, 15 L of methanol was added and five extractions with 20 L of dichloromethane were carried out. The dichloromethane extracts were pooled and concentrated under vacuum to 15 L.

Methanol (150 ml) was added and the solution was passed through a column containing 13 kg of neutral alumina eluting with dichloromethane-methanol 99:1 v/v. Fractions containing paclitaxel were collected and concentrated under vacuum to 5 L.

The concentrated solution was charged on a column containing 9 kg of silica gel and eluted with dichloromethane-methanol 99:1 v/v. After the elution of polar impurities, 220 L of fractions containing paclitaxel were collected, pooled and evaporated under vacuum in order to obtain a soft residue (190 g).

The residue was dissolved in 400 ml of acetone to form an acetone-residue which was column chromatographed over 9 kg of silica gel eluting with n-hexane-acetone 4:1. Fractions containing paclitaxel were collected and purified again by column chromatography over silica gel eluting with t-butyl acetate, as described in Example 2. After crystallization from the mixture with cyclohexane-acetone 1:1 and drying at 55° C., 18.5 g of paclitaxel having a purity greater than 99% were obtained.

While the foregoing description and drawings may represent preferred embodiments of the present invention, it should be understood that various additions, modifications, and substitutions may be made therein without departing from the spirit and scope of the present invention as defined in the accompanying claims. In particular, it will be clear to those skilled in the art that the present invention may be embodied in other specific forms, structures, arrangements, and proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims and not limited to the foregoing description.

We claim:

1. A method for obtaining paclitaxel from plants containing paclitaxel and of the Taxaceae family, said method comprising:
   (a) preparing a paclitaxel extract by extracting paclitaxel from a plant material;
   (b) separating paclitaxel from the paclitaxel extract using a first column chromatography system comprising a first stationary phase and a first eluting solvent to obtain at least one fraction containing paclitaxel;
   (c) separating paclitaxel from the at least one fraction obtained in step (b) using a second column chromatography system comprising a second stationary phase comprising neutral alumina and a second eluting solvent to obtain at least one fraction containing paclitaxel;
   (d) separating paclitaxel from the at least one fraction obtained in step (c) using a third column chromatography system comprising a third stationary phase and a third eluting solvent to obtain at least one fraction containing paclitaxel;
   (e) separating paclitaxel from the at least one fraction obtained in step (d) using a fourth column chromatography system comprising a fourth stationary phase and a fourth eluting solvent to remove at least cephalomannine and to obtain at least one fraction containing paclitaxel; and
   (f) crystallizing the paclitaxel contained in the at least one fraction obtained in step (e) using a crystallizing solvent to obtain paclitaxel crystals,
   wherein the first, second or third eluting solvent comprises dichloromethane.

2. The method of claim 1, further comprising drying the paclitaxel crystals obtained in step (f).

3. The method of claim 1, wherein the plant material is obtained from plant parts.

4. The method of claim 3, wherein the plant material extract is prepared by extracting the plant material comprising about 40 to about 60 w/w percent aerial parts and about 60 to about 40 w/w percent roots.

5. The method of claim 1, wherein the plant material comprises plant material obtained from *Taxus media*, *T.x media* "Henryi," *T.x media* "Runyan," *T. cuspidata*, *T.x media* "Halloran," *T.x media* "Hatfield," *T.x media* "Hicksii," *T.x media* "Tauntonii," *T.x media* "Dark Green Spreader," *T.x media* "Wardii," *T.x media* "Brownii," *T.x media* "Densiformis," *T.x media* "Nigra," *T.x cuspidata* "Brevifolia," or *T. cuspidata* "Spreader."

6. The method of claim 1, wherein the first, third, or fourth stationary phase comprises silica gel.

7. The method of claim 1, wherein the first, second or third eluting solvent comprises acetone, dichloromethane, methanol, n-hexane, t-butyl acetate, chloroform, or ethyl acetate.

8. The method of claim 1, wherein the first eluting solvent comprises dichloromethane and methanol.

9. The method of claim 1, wherein the second eluting solvent comprises acetone.

10. The method of claim 1, wherein the third eluting solvent comprises n-hexane and acetone.

11. The method of claim 1, wherein the fourth eluting solvent comprises t-butyl acetate, i-butyl acetate, n-butyl formate, i-butyl formate, t-butyl formate, or s-butyl formate.

12. The method of claim 1, wherein the crystallizing solvent comprises cyclohexane and acetone.

13. A method for obtaining paclitaxel from plants containing paclitaxel and of the Taxaceae family, said method comprising:
   (a) preparing a paclitaxel extract by extracting paclitaxel from a plant material;
   (b) separating paclitaxel from the paclitaxel extract comprising:
      (i) using a first column chromatography system comprising a first stationary phase and a first eluting solvent to obtain at least one fraction containing paclitaxel and
      (ii) removing the first eluting solvent from the at least one fraction obtained in step (b)(i) to form a first residue;
   (c) separating paclitaxel from the first residue obtained in step (b)(ii) comprising
      (i) using a second column chromatography system comprising a second stationary phase comprising neutral alumina and a second eluting solvent to obtain at least one fraction containing paclitaxel from the first residue, and
      (ii) removing the second eluting solvent from the at least one fraction obtained in step (c)(i) to form a second residue;
   (d) separating paclitaxel from the second residue obtained in step (c)(ii) comprising
      (i) using a third column chromatography system comprising a third stationary phase and a third eluting solvent to obtain at least one fraction containing paclitaxel from the second residue, and
      (ii) removing the third eluting solvent from the at least one fraction obtained in step (d)(i) to form a third residue;
   (e) separating paclitaxel from the third residue obtained in step (d)(ii) comprising (i) using a fourth column chromatography system comprising a fourth stationary phase and a fourth eluting solvent to obtain at least one fraction containing paclitaxel from the third residue, and (ii) removing the fourth eluting solvent from the third residue obtained in step (e)(i) to form a fourth residue; and (f) crystallizing paclitaxel from the fourth residue obtained in step (e)(ii) using a crystallizing solvent to obtain paclitaxel crystals, wherein the first, second or third eluting solvent comprises dichloromethane.

14. The method of claim 13 wherein in step (e) at least cephalomannine is removed from the third residue.

15. The method of claim 13, wherein the first eluting solvent is removed by subjecting the at least one fraction obtained in step (b)(i) to reduced pressure.

16. The method of claim 13, wherein the second eluting solvent is removed by subjecting the at least one fraction obtained in step (c)(i) to reduced pressure.

17. The method of claim 13, wherein the third eluting solvent is removed by subjecting the at least one fraction obtained in step (d)(i) to reduced pressure.

18. The method of claim 13, wherein the fourth eluting solvent is removed by subjecting the at least one fraction obtained in step (e)(i) to reduced pressure.

19. The method of claim 13, further comprising drying the paclitaxel crystals obtained in step (f).

20. The method of claim 19, wherein the paclitaxel crystals are dried under vacuum.

21. The method of claim 13, wherein the paclitaxel is extracted from the plant material using a first aqueous solvent.

22. The method of claim 21, wherein the first aqueous solvent comprises water and acetone.

23. The method of claim 13, wherein step (a) occurs at room temperature.

24. The method of claim 13, wherein more than one fraction is obtained in step (b)(i) and at least some of the fractions are combined before removing the first eluting solvent in step (b)(ii).

25. The method of claim 13, wherein more than one fraction is obtained in step (c)(i) and at least some of the fractions are combined before removing the second eluting solvent in step (c)(ii).

26. The method of claim 13, wherein more than one fraction is obtained in step (d)(i) and at least some of the fractions are combined before removing the third eluting solvent in step (d)(ii).

27. The method of claim 13, wherein more than one fraction is obtained in step (e)(i) and at least some of the fractions are combined before removing the fourth eluting solvent in step (e)(ii).

28. The method of claim 13, wherein the crystallizing of step (f) occurs over a 24 hour period.

29. The method of claim 13, wherein the crystallizing of step (f) occurs at room temperature.

30. The method of claim 13, wherein the plant material is obtained from plant parts.

31. The method of claim 30, wherein the plant material extract is prepared by extracting the plant material from plant parts comprising about 40 to about 60 w/w percent aerial parts and about 60 to about 40 w/w percent roots.

32. The method of claim 13, wherein the plant material comprises plant material obtained from *Taxus media, T.x media* "Henryi," *T.x media* "Runyan," *T. cuspidata, T.x media* "Halloran," *T.x media* "Hatfield," *T.x media* "Hicksii," *T.x media* "Tauntonii," *T.x media* "Dark Green Spreader," *T.x media* "Wardii," *T.x media* "Brownii," *T.x media* "Densiformis," *T.x media* "Nigra," *T.x cuspidata* "Brevifolia," or *T. cuspidata* "Spreader.".

33. The method of claim 13, wherein the first, third, or fourth stationary phase comprises silica gel.

34. The method of claim 13, wherein the first, second or third eluting solvent comprises acetone, dichloromethane, methanol, n-hexane, t-butyl acetate, chloroform, or ethyl acetate.

35. The method of claim 13, wherein the first eluting solvent comprise dichloromethane and methanol.

36. The method of claim 13, wherein the second eluting solvent comprise acetone.

37. The method of claim 13, wherein the third eluting solvent comprise n-hexane, and acetone.

38. The method of claim 13, wherein the fourth eluting solvent comprises t-butyl acetate, i-butyl acetate, n-butyl formate, i-butyl formate, t-butyl formate, or s-butyl formate.

39. The method of claim 13, wherein the crystallizing solvent comprises cyclohexane and acetone.

40. A method for obtaining paclitaxel from *Taxus media*, said method comprising:

(a) preparing a plant material extract from the *Taxus media* by extracting the plant material with an aqueous solvent comprising about 40 to about 60 v/v percent acetone at room temperature;

(b) preparing a paclitaxel extract by extracting paclitaxel from the plant material extract obtained in (a);

(c) separating paclitaxel from the paclitaxel extract comprising (i) using a first chromatography system comprising silica gel as a stationary phase and an eluting solvent comprising dichloromethane alone or a mixture of dichloromethane and methanol to obtain at least one fraction containing paclitaxel, and (ii) subjecting the at least one fraction obtained in step (c)(i) to reduced pressure to remove the dichloromethane and/or methanol;

(d) separating paclitaxel from the at least one fraction obtained in step (c)(ii) comprising (i) using a second column chromatography system comprising neutral alumina as a stationary phase and an eluting solvent comprising acetone to obtain at least one fraction containing paclitaxel, and (ii) subjecting the at least one fraction obtained in step (d)(i) to reduced pressure to remove the acetone;

(e) separating paclitaxel from the at least one fraction obtained in step (d)(ii) comprising (i) using a third column chromatography system comprising silica gel as a stationary phase and an eluting solvent comprising a mixture of n-hexane and acetone and to obtain at least one fraction containing paclitaxel, and (ii) subjecting the at least one fraction obtained in step (e)(i) to reduced pressure to remove the n-hexane and acetone;

(f) separating paclitaxel from the at least one fraction obtained in step (e)(ii) comprising (i) using a fourth column chromatography system comprising silica gel as a stationary phase and an eluting solvent comprising t-butyl acetate to remove at least cephalomannine and to obtain at least one fraction containing paclitaxel, and (ii) subjecting the at least one fraction obtained in step (f)(i) to reduced pressure to remove the t-butyl acetate;

(g) crystallizing the at least one fraction obtained in step (f)(i) over a 24 hour period using a mixture of cyclohexane and acetone as the crystallizing solvent at room temperature to obtain paclitaxel crystals; and (h) drying the paclitaxel crystals obtained in (g) under vacuum for 48 hours.

41. The method of claim 40, wherein the preparation of the paclitaxel extract in step (b) further comprises:
   (a) concentrating the plant material extract under reduced pressure to remove the acetone to form a concentrate;
   (b) diluting the concentrate with methyl alcohol;
   (c) extracting the concentrate with dichloromethane to form a dichloromethane extract; and
   (d) concentrating the dichloromethane extract under reduced pressure to form the paclitaxel extract.

42. A method for obtaining paclitaxel from *Taxus media*, said method comprising:
   (a) preparing a plant material extract from the *Taxus media* by extracting the plant material with an aqueous solvent comprising about 40 to about 60 v/v percent acetone at room temperature;
   (b) preparing a paclitaxel extract by extracting paclitaxel from the plant material extract obtained in (a);
   (c) separating paclitaxel from the paclitaxel extract comprising
      (i) using a first chromatography system comprising silica gel as a stationary phase and an eluting solvent comprising dichloromethane and methanol to obtain at least one fraction containing paclitaxel,
      (ii) subjecting the at least one fraction obtained in step (c)(i) to reduced pressure to obtain a residue, and
      (iii) dissolving the residue obtained in step (c)(ii) in acetone to obtain an acetone-residue composition;
   (d) separating paclitaxel from the acetone-residue composition obtained in step (c)(iii) comprising
      (i) using a second column chromatography system comprising neutral alumina as a stationary phase and an eluting solvent comprising acetone to obtain at least one fraction containing paclitaxel, and
      (ii) subjecting the at least one fraction obtained in step (d)(i) to reduced pressure to remove the acetone;
   (e) separating paclitaxel from the at least one fraction obtained in step (d)(ii) comprising
      (i) using a third column chromatography system comprising silica gel as a stationary phase and an eluting solvent comprising n-hexane and acetone to obtain at least one fraction containing paclitaxel, and
      (ii) subjecting the at least one fraction obtained in step (e)(i) to reduced pressure to remove the n-hexane and acetone;
   (f) separating paclitaxel from the at least one fraction obtained in step (e)(ii) comprising
      (i) using a fourth column chromatography system comprising silica gel as a stationary phase and an eluting solvent comprising t-butyl acetate to remove at least cephalomannine and to obtain at least one fraction containing paclitaxel, and
      (ii) subjecting the at least one fraction obtained in step (f)(i) to reduced pressure to remove the t-butyl acetate;
   (g) crystallizing the at least one fraction obtained in step (f)(ii) over a 24 hour period using a mixture of cyclohexane and acetone as the crystallizing solvent at room temperature to obtain paclitaxel crystals; and
   (h) drying the paclitaxel crystals obtained in (g) under vacuum for 48 hours.

43. The method of claim 42, wherein the *Taxus media* comprises *T. media Hicksii*.

44. A method for obtaining paclitaxel from *Taxus media*, said method comprising:
   (a) preparing a plant material extract from the *Taxus media* by extracting the plant material with an aqueous solution comprising about 40 to about 60 v/v percent acetone at room temperature;
   (b) preparing a paclitaxel extract by extracting paclitaxel from the plant material extract obtained in (a);
   (c) separating paclitaxel from the paclitaxel extract comprising
      (i) using a first chromatography system comprising neutral alumina as a stationary phase and an eluting solvent comprising dichloromethane and methanol to obtain at least one fraction containing paclitaxel and
      (ii) subjecting the at least one fraction obtained in step (c)(i) to reduced pressure to remove the dichloromethane and methanol;
   (d) separating paclitaxel from the at least one fraction obtained in step (c)(ii) comprising
      (i) using a second column chromatography system comprising silica gel as a stationary phase and an eluting solvent comprising dichloromethane and methanol to obtain at least one fraction containing paclitaxel,
      (ii) subjecting the at least one fraction obtained in step (d)(i) to reduced pressure to obtain a residue, and
      (iii) dissolving the residue obtained in step (d)(ii) in acetone to obtain an acetone-residue composition;
   (e) separating paclitaxel from the acetone-residue composition obtained in step (d)(iii) comprising
      (i) using a third column chromatography system comprising silica gel as a stationary phase and an eluting solvent comprising n-hexane and acetone to obtain at least one fraction containing paclitaxel, and
      (ii) subjecting the at least one fraction obtained in step (e)(i) to reduced pressure to remove the mixture of n-hexane and acetone;
   (f) separating paclitaxel from the at least one fraction obtained in step (e)(ii) comprising
      (i) using a fourth column chromatography system comprising silica gel as a stationary phase and an eluting solvent comprising a t-butyl acetate to remove at least cephalomannine and to obtain at least one fraction containing paclitaxel, and
      (ii) subjecting the at least one fraction obtained in step (f)(i) to reduced pressure to remove the t-butyl acetate;
   (g) crystallizing the at least one fraction obtained in step (f)(ii) over a 24 hour period using a mixture of cyclohexane and acetone as the crystallizing solvent at room temperature to obtain paclitaxel crystals; and
   (h) drying the paclitaxel crystals obtained in (g) under vacuum for 48 hours.

45. The method of claim 44, wherein the *Taxus media* comprises *T. media* "dark green spreader".

46. A method for obtaining paclitaxel from a plant containing paclitaxel and of the Taxaceae family, said method comprising:
   (a) preparing a plant material extract by extracting a plant material from the plant with an aqueous solvent comprising about 40 to about 60 v/v percent acetone at room temperature;
   (b) preparing a paclitaxel extract by extracting paclitaxel from the plant material extract obtained in (a);

(c) separating paclitaxel from the paclitaxel extract comprising
　(i) using a first chromatography system comprising silica gel as a stationary phase and an eluting solvent comprising dichloromethane alone or a mixture of dichloromethane and methanol to obtain at least one fraction containing paclitaxel, and
　(ii) subjecting the at least one fraction obtained in step (c)(i) to reduced pressure to remove the dichloromethane and/or methanol;
(d) separating paclitaxel from the at least one fraction obtained in step (c)(ii) comprising
　(i) using a second column chromatography system comprising neutral alumina as a stationary phase and an eluting solvent comprising acetone to obtain at least one fraction containing paclitaxel, and
　(ii) subjecting the at least one fraction obtained in step (d)(i) to reduced pressure to remove the acetone;
(e) separating paclitaxel from the at least one fraction obtained in step (d)(ii) comprising
　(i) using a third column chromatography system comprising silica gel as a stationary phase and an eluting solvent comprising a mixture of n-hexane and acetone and to obtain at least one fraction containing paclitaxel, and
　(ii) subjecting the at least one fraction obtained in step (e)(i) to reduced pressure to remove the n-hexane and acetone;
(f) separating paclitaxel from the at least one fraction obtained in step (e)(ii) comprising
　(i) using a fourth column chromatography system comprising silica gel as a stationary phase and an eluting solvent comprising t-butyl acetate to remove at least cephalomannine and to obtain at least one fraction containing paclitaxel, and
　(ii) subjecting the at least one fraction obtained in step (f)(i) to reduced pressure to remove the t-butyl acetate;
(g) crystallizing the at least one fraction obtained in step (f)(i) over a 24 hour period using a mixture of cyclohexane and acetone as the crystallizing solvent at room temperature to obtain paclitaxel crystals; and
(h) drying the paclitaxel crystals obtained in (g) under vacuum for 48 hours.

47. The method of claim 46, wherein the preparation of the paclitaxel extract in step (b) further comprises:
　(a) concentrating the plant material extract under reduced pressure to remove the acetone to form a concentrate;
　(b) diluting the concentrate with methyl alcohol;
　(c) extracting the concentrate with dichloromethane to form a dichloromethane extract; and
　(d) concentrating the dichloromethane extract under reduced pressure to form the paclitaxel extract.

48. The method of claim 46, wherein the plant is *Taxus media*, *T.x media* "Henryi," *T.x media* "Runyan," *T. cuspidata*, *T.x media* "Halloran," *T.x media* "Hatfield," *T.x media* "Hicksii," *T.x media* "Tauntonji," *T.x media* "Dark Green Spreader," *T.x media* "Wardii," *T.x media* "Brownii," *T.x media* "Densiformis," *T.x media* "Nigra," *T.x cuspidata* "Brevifolia," or *T. cuspidata* "Spreader."

49. A method for obtaining paclitaxel from a plant containing paclitaxel and of the Taxaceae family, said method comprising:
　(a) preparing a plant material extract by extracting a plant material from the plant with an aqueous solvent comprising about 40 to about 60 v/v percent acetone at room temperature;
　(b) preparing a paclitaxel extract by extracting paclitaxel from the plant material extract obtained in (a);
　(c) separating paclitaxel from the paclitaxel extract comprising
　　(i) using a first chromatography system comprising silica gel as a stationary phase and an eluting solvent comprising dichloromethane and methanol to obtain at least one fraction containing paclitaxel,
　　(ii) subjecting the at least one fraction obtained in step (c)(i) to reduced pressure to obtain a residue, and
　　(iii) dissolving the residue obtained in step (c)(ii) in acetone to obtain an acetone-residue composition;
　(d) separating paclitaxel from the acetone-residue composition obtained in step (c)(iii) comprising
　　(i) using a second column chromatography system comprising neutral alumina as a stationary phase and an eluting solvent comprising acetone to obtain at least one fraction containing paclitaxel, and
　　(ii) subjecting the at least one fraction obtained in step (d)(i) to reduced pressure to remove the acetone;
　(e) separating paclitaxel from the at least one fraction obtained in step (d)(ii) comprising
　　(i) using a third column chromatography system comprising silica gel as a stationary phase and an eluting solvent comprising n-hexane and acetone to obtain at least one fraction containing paclitaxel, and
　　(ii) subjecting the at least one fraction obtained in step (e)(i) to reduced pressure to remove the n-hexane and acetone;
　(f) separating paclitaxel from the at least one fraction obtained in step (e)(ii) comprising
　　(i) using a fourth column chromatography system comprising silica gel as a stationary phase and an eluting solvent comprising t-butyl acetate to remove at least cephalomannine and to obtain at least one fraction containing paclitaxel, and
　　(ii) subjecting the at least one fraction obtained in step (f)(i) to reduced pressure to remove the t-butyl acetate;
　(g) crystallizing the at least one fraction obtained in step (f)(ii) over a 24 hour period using a mixture of cyclohexane and acetone as the crystallizing solvent at room temperature to obtain paclitaxel crystals; and
　(h) drying the paclitaxel crystals obtained in (g) under vacuum for 48 hours.

50. The method of claim 49, wherein the plant is *Taxus media*, *T.x media* "Henryi," *T.x media* "Runyan," *T. cuspidata*, *T.x media* "Halloran," *T.x media* "Hatfield," *T.x media* "Hicksii," *T.x media* "Tauntonii," *T.x media* "Dark Green Spreader," *T.x media* "Wardii," *T.x media* "Brownii," *T.x media* "Densiformis," *T.x media* "Nigra," *T.x cuspidata* "Brevifolia," or *T. cuspidata* "Spreader."

51. A method for obtaining paclitaxel from a plant containing paclitaxel and of the Taxaceae family, said method comprising:
　(a) preparing a plant material extract by extracting a plant material from the plant with an aqueous solvent comprising about 40 to about 60 v/v percent acetone at room temperature;
　(b) preparing a paclitaxel extract by extracting paclitaxel from the plant material extract obtained in (a);
　(c) separating paclitaxel from the paclitaxel extract comprising
　　(i) using a first chromatography system comprising neutral alumina as a stationary phase and an eluting solvent comprising dichloromethane and methanol to obtain at least one fraction containing paclitaxel and (ii) subjecting the at least one fraction obtained in step (c)(i) to reduced pressure to remove the dichloromethane and methanol;

(d) separating paclitaxel from the at least one fraction obtained in step (c)(ii) comprising
  (i) using a second column chromatography system comprising silica gel as a stationary phase and an eluting solvent comprising dichloromethane and methanol to obtain at least one fraction containing paclitaxel,
  (ii) subjecting the at least one fraction obtained in step (d)(i) to reduced pressure to obtain a residue, and
  (iii) dissolving the residue obtained in step (d)(ii) in acetone to obtain an acetone-residue composition;

(e) separating paclitaxel from the acetone-residue composition obtained in step (d)(iii) comprising
  (i) using a third column chromatography system comprising silica gel as a stationary phase and an eluting solvent comprising n-hexane and acetone to obtain at least one fraction containing paclitaxel, and
  (ii) subjecting the at least one fraction obtained in step (e)(i) to reduced pressure to remove the mixture of n-hexane and acetone;

(f) separating paclitaxel from the at least one fraction obtained in step (e)(ii) comprising
  (i) using a fourth column chromatography system comprising silica gel as a stationary phase and an eluting solvent comprising a t-butyl acetate to remove at least cephalomannine and to obtain at least one fraction containing paclitaxel, and
  (ii) subjecting the at least one fraction obtained in step (f)(i) to reduced pressure to remove the t-butyl acetate;

(g) crystallizing the at least one fraction obtained in step (f)(ii) over a 24 hour period using a mixture of cyclohexane and acetone as the crystallizing solvent at room temperature to obtain paclitaxel crystals; and (h) drying the paclitaxel crystals obtained in (g) under vacuum for 48 hours.

52. The method of claim 51, wherein the plant is *Taxus media, T.x media* "Henryi," *T.x media* "Runyan," *T. cuspidata, T.x media* "Halloran," *T.x media* "Hatfield," *T.x media* "Hicksii," *T.x media* "Tauntonii," *T.x media* "Dark Green Spreader," *T.x media* "Wardii ," *T.x media* "Brownii," *T.x media* "Densiformis," *T.x media* "Nigra," *T.x cuspidata* "Brevifolia," or *T. cuspidata* "Spreader."

* * * * *